US00PP33039P2

(12) United States Plant Patent
Walker et al.

(10) Patent No.: US PP33,039 P2
(45) Date of Patent: May 11, 2021

(54) GRAPEVINE PLANT NAMED 'PASEANTE NOIR'

(50) Latin Name: ***Vitis vinifera* L.**
Varietal Denomination: Paseante Noir

(71) Applicant: The Regents of the University of California, Oakland, CA (US)

(72) Inventors: Michael Andrew Walker, Davis, CA (US); Alan C. Tenscher, Davis, CA (US); Summaira Riaz, Davis, CA (US); Ninfa Romero, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/602,587

(22) Filed: Nov. 5, 2019

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./205
CPC ..... A01H 5/0812
See application file for complete search history.

(56) References Cited

PUBLICATIONS

The Apr. 1, 2014 Test Agreement For Grape vines (No. 2015-5011) between Silverado Vineyards and The Regents of the University of California, 7 pages.
The Apr. 19, 2019 Test Agreement For Grapevines (No. 2019-5008) between Frog's Leap Winery and The Regents of the University of California, 6 pages.
The Aug. 1, 2014 Test Agreement For Trees/Rootstocks (No. 2015-5010) between Caymus Vineyards and The Regents of the University of California, 7 pages.
The May 1, 2014 Test Agreement For Grape vines (No. 2016-5008) between Ben R. Drake Enterprises, Inc. and The Regents of the University of California, 7 pages.
The May 16, 2017 Test Agreement For Grapevines (No. 2017-5008) between Wonderful Nurseries, LLC and The Regents of the University of California, 7 pages.
The May 17, 2017 Test Agreement For Grapevines (No. 2017-5011) between Sunridge Nurseries, Inc. and The Regents of the University of California, 6 pages.
The May 18, 2017 Test Agreement For Grapevines (No. 2017-5009) between Novavine and The Regents of the University of California, 6 pages.
The May 24, 2017 Test Agreement For Grapevines (No. 2017-5010) between Sutter Home Winery, Inc. and The Regents of the University of California, 7 pages.

*Primary Examiner* — Kent L Bell
(74) *Attorney, Agent, or Firm* — McKee, Voorhees & Sease, PLC

(57) ABSTRACT

A new and distinct variety of grapevine plant named 'Paseante Noir', particularly selected for its high resistance to Pierce's disease, as well as quality of fruit and wines produced is disclosed.

6 Drawing Sheets

Latin name:
Botanical classification: *Vitis vinifera* L.
Varietal denomination: The varietal denomination of the claimed variety of grapevine plant is 'Paseante Noir'.

BACKGROUND OF THE INVENTION

Pierce's disease (PD) is common across the southern United States from Virginia to northern California. It is also common across Mexico and Central America. The disease is caused by the bacterium *Xylella fastidiosa*, which is hosted by a very wide range of native and ornamental plants. The bacterium is spread by xylem feeding insects as vectors, primarily sharpshooters. PD is one of the few diseases that rapidly kills wine, table, and raisin grape cultivars of the cultivated grape, *Vitis vinifera*. Vector populations can be limited with insecticides, but these are difficult to use near their typically riparian native habitat or in the ornamental landscapes in which they flourish. Breeding for PD resistance has been active for over 70 years, but progress has been very slow due to a poor understanding of the germplasm and the typically multigenic nature of the resistance in most of the resistant grape species. The two most commonly grown PD resistant varieties, 'Blanc du Bois' and 'Lenoir' ('Lenoir' is also known as 'Black Spanish' or 'Jacquet'), are $F_1$ hybrids between *V. vinifera* cultivars and resistant American grape species from the southern United States, and are therefore only about 50% of *V. vinifera*. 'Blanc du Bois' and 'Lenoir' produce wines with lower quality than *V. vinifera* wine grape varieties, and they are tolerant of, rather than resistant to, *X. fastidiosa* infection, which results in their potential to expand areas damaged by PD due to their ability to act as host plants for the bacteria and vectors. Neither 'Blanc du Bois' nor 'Lenoir' are patented.

Grapevine is an important and valuable crop. Accordingly, there is a need for new varieties of grapevine plant. In particular, there is a need for improved varieties of grapevine plant that produce high quality fruit for winemaking and are resistant to Pierce's disease.

SUMMARY OF THE INVENTION

In order to meet these needs, the present invention is directed to an improved variety of grapevine plant. In particular, the invention relates to a new and distinct variety of grapevine plant (*Vitis vinifera* L.), which has been denominated as 'Paseante Noir'. Grapevine plant variety 'Paseante Noir' possesses very strong resistance to the bacterial causal agent of Pierce's disease (PD), and produces very high quality fruit and wines therefrom that are indistinguishable from the widely grown European wine grape cultivars. Other PD resistant cultivars are known, but their fruit and winemaking quality are poor in comparison to 'Paseante Noir' and their resistance is much lower.

In particular, grapevine plant variety 'Paseante Noir' is a red wine grape selection that is about 97% *V. vinifera* (including 50% 'Zinfandel', 25% 'Petite Sirah', and 12.5% 'Cabernet Sauvignon'). In comparison, the two most commonly grown PD resistant varieties, 'Blanc du Bois' and 'Lenoir', are only about 50% of *V. vinifera*. 'Paseante Noir' is highly resistant to PD, as established in field trials conducted in Ojai and along the Napa River in California. 'Paseante Noir' blooms relatively late, but ripens midseason. The berries are medium and the clusters are well-filled and relatively large. Although 'Paseante Noir' is spur fruitful, it typically has only one cluster per shoot and is more productive with cane pruning. Wines made from fruit of 'Paseante Noir' grown in Davis and Napa, Calif. may be described as: 'medium dark red with purple'; 'berry pie', 'cassis', 'black olive', 'herbal', 'dried hay', 'coffee', 'vegetal like Cabernet Sauvignon', 'licorice', 'round', 'moderate tannins', and 'soft finish'.

Pedigree and Breeding History

The development of this new grapevine variety is in part a result of the discovery of a single dominant gene for resistance to *Xylella fastidiosa*, the bacterial causal agent of Pierce's disease (PD). The source of the PD resistance is a form of *V. arizonica* ('b43-17') that appears to have some *V. candicans* parentage and is from Monterrey, Mexico. 'b43-17' was crossed to the susceptible *V. rupestris* 'A. de Serres' to create the F8909 population. Neither 'b43-17' nor 'A. de Serres' are patented. The resistance from 'b43-17' was found to be inherited as a single dominant gene (locus), and this resistance gene, PdRl, was genetically mapped using the F8909 population by a grapevine breeding program. Tightly linked simple sequence repeat (SSR) markers were developed and were used in marker-assisted selection to exclude susceptible plants from evaluation in each round of selection. All the progeny with PdRl were tested for PD resistance and only those with strong resistance were considered for use as parents. Potential parents were also screened for fruit quality over generations and only those with good quality fruit and that appeared like *V. vinifera* were selected.

Line 'F8909-08' from the F8909 population was crossed to 'P79-101', a highly susceptible, advanced *V. vinifera* table grape selection from a grape breeding program. The resulting 'F8909-08' X 'P79-101' $F_1$ generation and progeny thereof were screened with the SSR markers for resistance to *X. fastidiosa* under greenhouse conditions. A highly resistant selection from the 'F8909-08' X 'P79-101' cross, '00504-20', was crossed to another *V. vinifera* table grape from a breeding program, 'B52-89', to create 'A81-138', which was also selected for its very high resistance to PD. 'A81-138' was then used to cross to *V. vinifera* wine grapes for several generations of modified backcrossing to obtain the candidate selection '09331-047', which was later named as 'Paseante Noir'. None of the parents across the multiple backcross generations are patented. These backcrosses were modified because of the high heterozygosity and recessive load found in grapes. Hence, to avoid exposure of deleterious recessive alleles, each generation of backcrossing was to a different and unrelated high quality *V. vinifera* cultivar.

Accordingly, the parentage of 'Paseante Noir' is '07355-020' ('U0505-01' ('A81-138' X 'Cabernet Sauvignon') X 'Petite Sirah') X *V. vinifera* 'Zinfandel'. 'Paseante Noir' was particularly selected for its high resistance to Pierce's disease, as well as the quality of its fruit and wines produced therefrom. It is distinguishable from its maternal parent by its relatively large leaves with distinctive lobing and relatively large teeth, and from its paternal parent by its strong resistance to *X. fastidiosa*.

BRIEF DESCRIPTION OF THE DRAWINGS

This new grapevine plant variety is illustrated by the accompanying photographs. The colors shown are as true as can be reasonably obtained by conventional photographic procedures. The photographs are of plants that are five to seven years old. Colors referred to are in reference to The Royal Horticultural Society Colour Charts Edition V.

FIG. 1 shows simple sequence repeat (SSR) marker data establishing a DNA fingerprint for 'Paseante Noir' with nine pure *Vitis vinifera* cultivars for comparison. Alleles for marker-assisted selection of the *Xylella fastidiosa* locus (PdRl) are shown in red.

DETAILED BOTANICAL DESCRIPTION

The following is a detailed description of the new grapevine plant variety designated as 'Paseante Noir', including the key differentiating characteristics of this variety and comparisons of characteristics of 'Paseante Noir' to other grapevine varieties. Unless otherwise indicated, evaluation data were taken from five- to seven-year-old plants, grown in Davis, Calif.

Classification:

*Family*.—Vitaceae.

*Botanical name*.—*Vitis vinifera* L.

*Common name*.—Grapevine.

*Variety name*.—'Paseante Noir'.

Parentage:

*Female parent*.—'07355-020' (unpatented).

*Male parent*.—'Zinfandel' (unpatented).

Plant:

*Berries*.—Medium to large, spherical, dark purple-black with light grey bloom.

*Clusters*.—Medium to large, long conical, loose to well-filled with looser and long shoulders.

*Leaves*.—Five-lobed with overlapping lobes, rectangular in outline, occasional teeth in the lateral sinuses, small short rounded teeth on leaf margin, glabrous adaxial surface, relatively dense short tomentum on abaxial surface, red-purple petioles and color diffuses into the veins.

*Shoot tips*.—Erect, green with white tomentum on upper leaves.

*Production*.—Blooms relatively late, ripens mid-season, more productive with cane pruning.

*Method of propagation*.—Vegetative propagation via woody or herbaceous cuttings, or budding and grafting to rootstock. 'Paseante Noir' has been asexually reproduced June 2009 at greenhouses at Orchard Park Dr. in Davis, Calif. from herbaceous cuttings. Any rootstock can be used with the variety. Most often it will be grown on rootstocks that resist grape phylloxera and or nematodes. In testing, selections were evaluated grafted on '1103P' rootstock which is not patented. It was chosen for ease of propagation and because it is widely used in California. The variety has been grafted on many other rootstocks for testing in field trials as well.

'Paseante Noir' has the highest form of resistance to *X. fastidiosa* coupled with the highest wine quality of any PD resistant wine grape yet produced. 'Paseante Noir' is selected for very high resistance, not the more commonly found tolerance, to prevent the production of host plants capable of further spreading PD to surrounding vineyards.

'Paseante Noir' has a very strong PD resistance and the highest wine quality of any currently used PD resistant wine grape. PD is one of the few diseases that kill susceptible grapevines. Two most popular PD resistant wine grape varieties, 'Blanc du Bois' and 'Lenoir' ('Lenoir' is also known as 'Black Spanish' or 'Jacquez'), were used as controls or standards in all testing so that the wine quality and resistance of the candidate variety could be compared to available PD resistant varieties used across the southern United States. It is noted that 'Blanc du Bois' and 'Lenoir' have relatively poor wine quality and are tolerant, not resistant, to PD. Neither 'Blanc du Bois' nor 'Lenoir' are patented.

Figure 2:
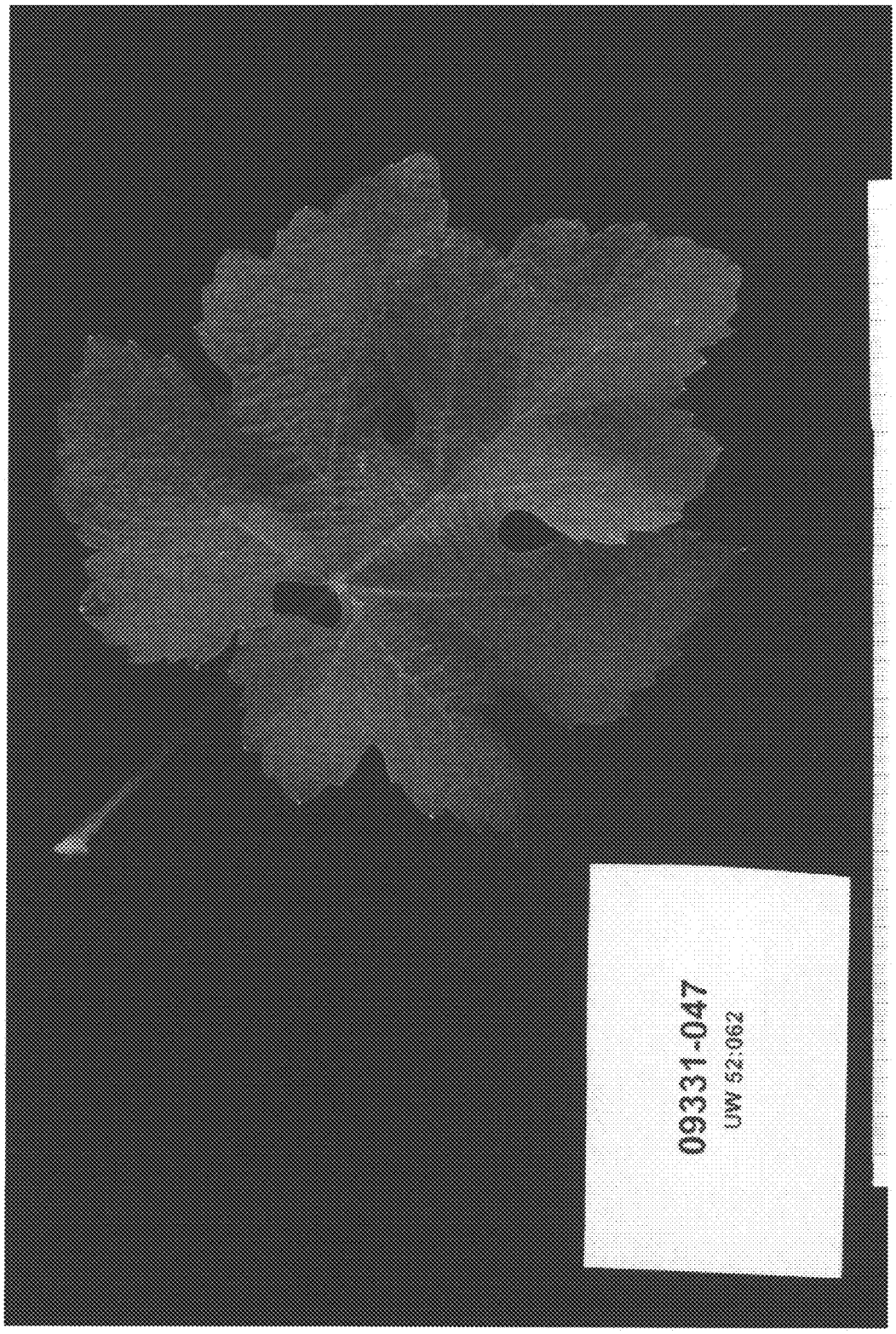
FIG. 2 illustrates the upper surface of a leaf of grapevine plant variety 'Paseante Noir'.
Figure 3:
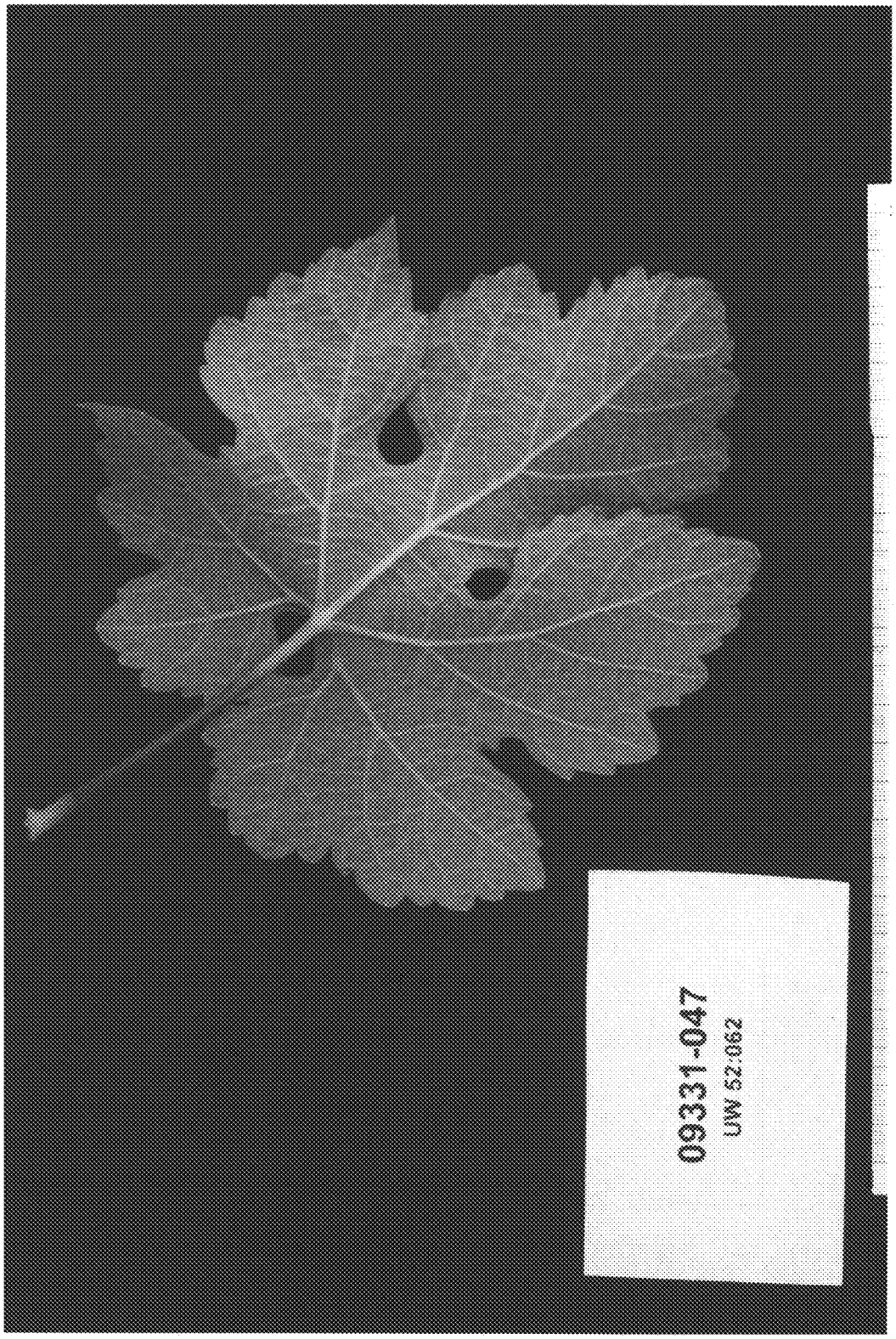
FIG. 3 illustrates the lower surface of a leaf of grapevine plant variety 'Paseante Noir'.
Figure 4:
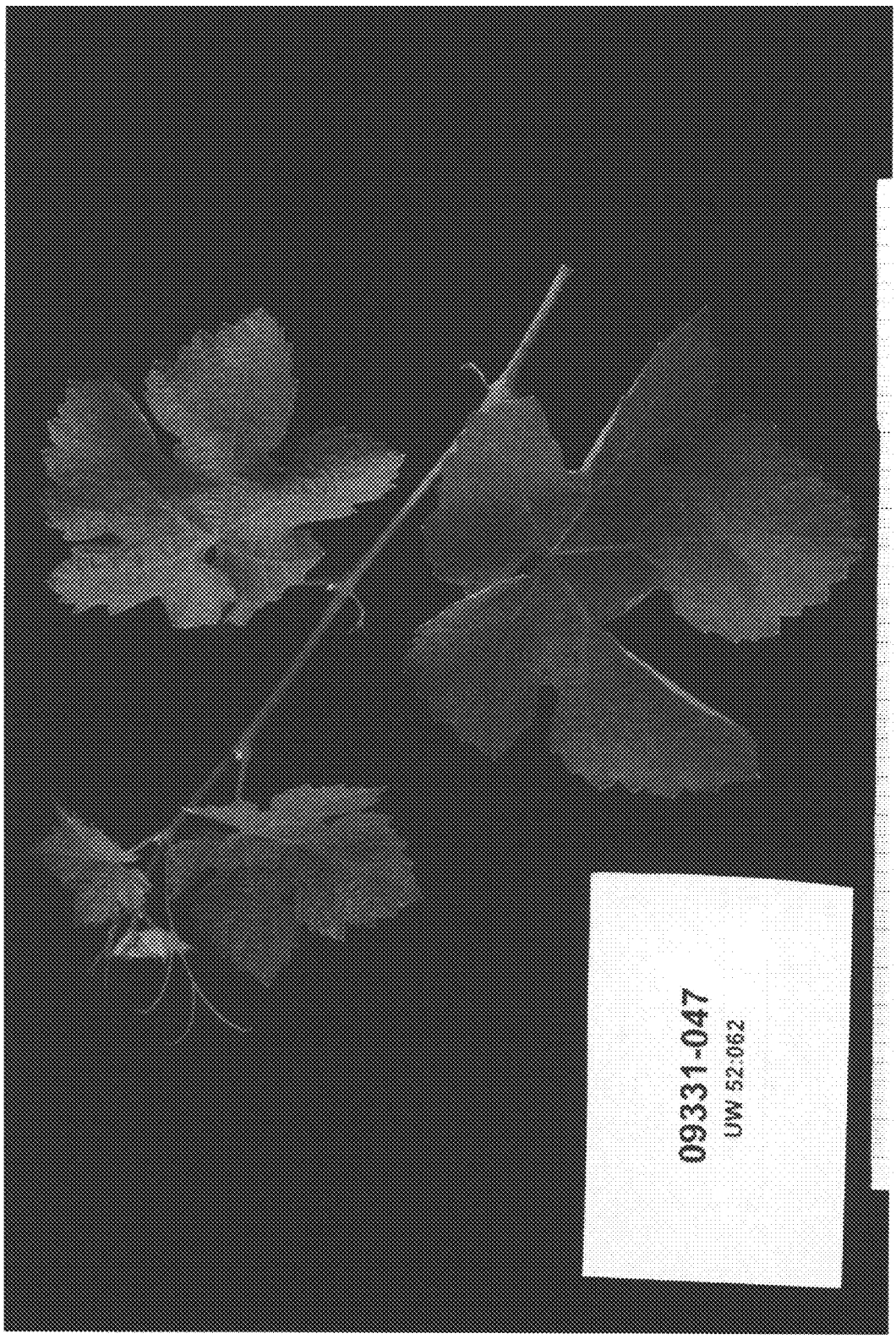
FIG. 4 illustrates a section of a shoot tip of grapevine plant variety 'Paseante Noir'.
Figure 5:
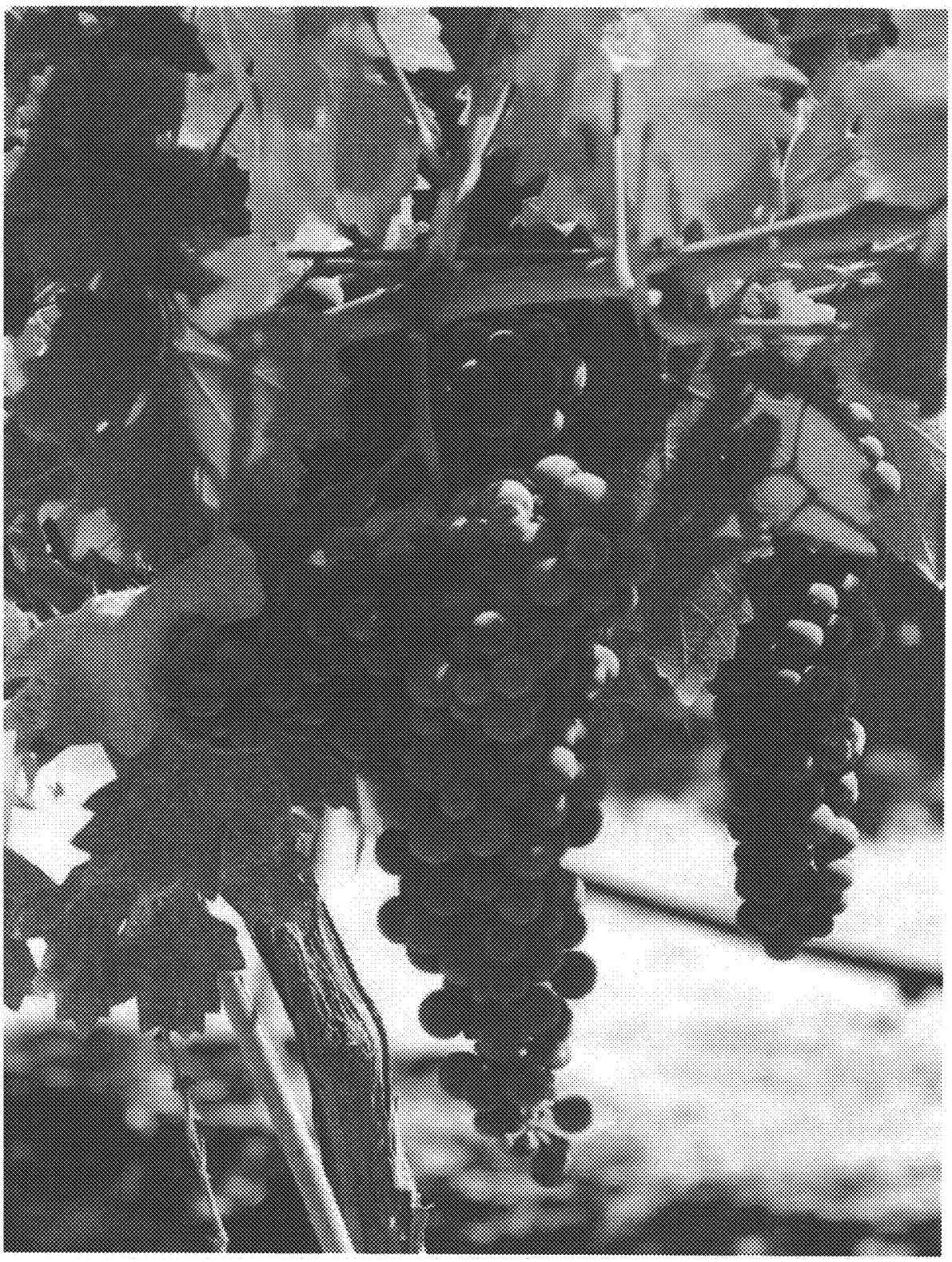
FIG. 5 illustrates a plant of grapevine plant variety 'Paseante Noir' bearing clusters of berries.
Figure 6:
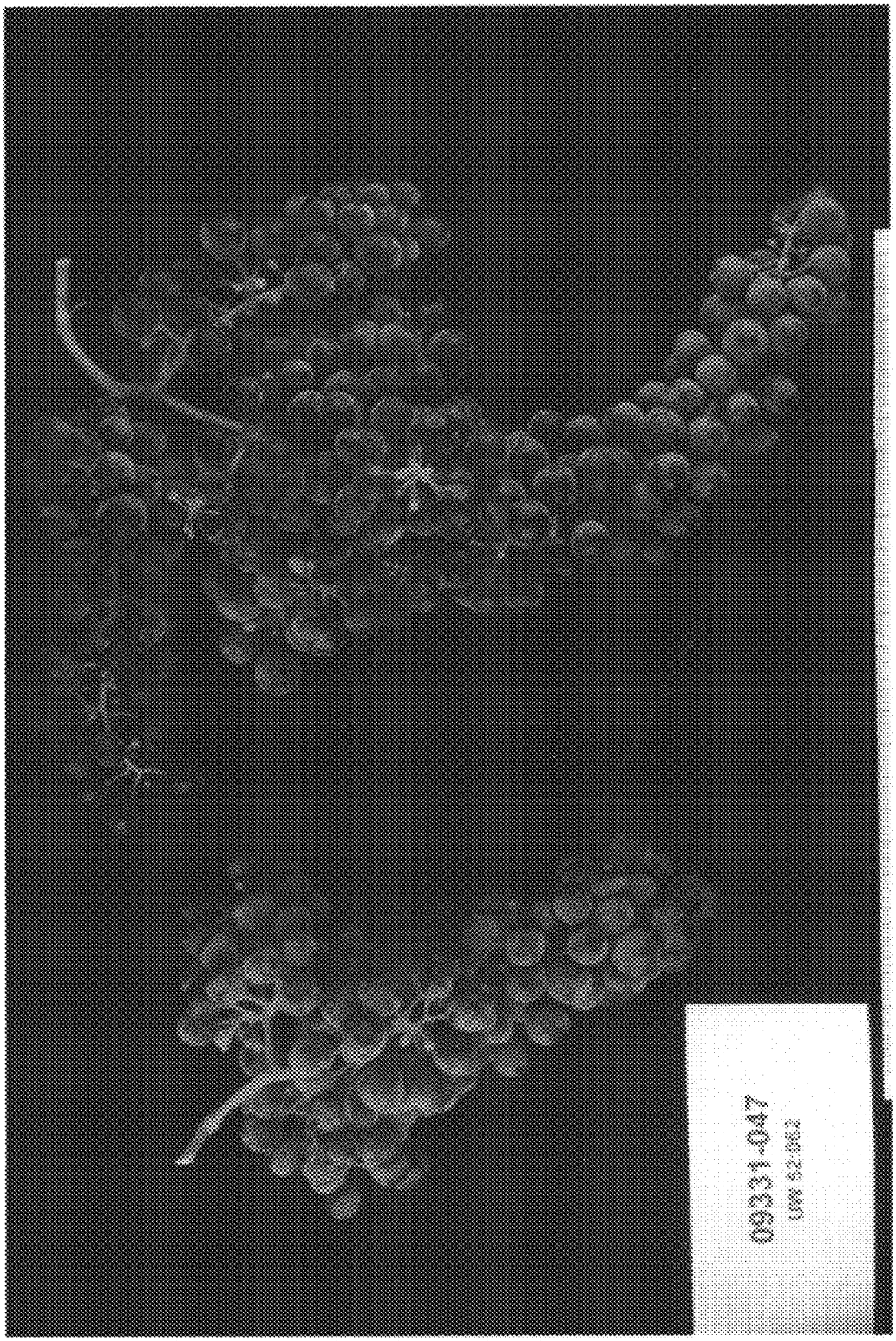
FIG. 6 illustrates a cluster of grapes of grapevine plant variety 'Paseante Noir'.

'Paseante Noir' has far better PD resistance and wine quality when compared with 'Blanc du Bois' and 'Lenoir'. In other words, 'Paseante Noir' combines very strong resistance to *X. fastidiosa* with the wine quality of internationally acclaimed wine grape cultivars. 'Paseante Noir' was selected as a variety that exhibits high resistance to *X. fastidiosa* and *V. vinifera*-like wine quality. The data presented below are intended to further characterize 'Paseante Noir'. The appearance of 'Paseante Noir' is illustrated in FIGS. 2-6, and further characteristics of 'Paseante Noir' are presented in Tables 1-8.

FIG. 1 presents the DNA fingerprinting profile for 'Paseante Noir' and nine pure *Vitis vinifera* cultivars for comparison with the standard set of internationally agreed-upon genetic markers. This SSR fingerprinting profile can be used for DNA-based identification.

Table 1 presents typical phenological data for 'Paseante Noir'. These data are for 2016, but the ranking of the selections in regard to an early cultivar ('Pinot noir') and a late cultivar ('Cabernet Sauvignon') have been typical over years. In general, 'Paseante Noir' is phenologically mid-season. Based on the percentage of *V. vinifera* in this plant and the nature of its parents, the variety is expected to grow in USDA Hardiness Zone 6-7.

TABLE 1

Average phenological states for 'Paseante Noir'. 'Cabernet Sauvignon' (late) and 'Pinot noir' (early) are included as comparisons.

| Cultivar | Budbreak | 50% bloom | 50% veraison | 24 °Brix |
|---|---|---|---|---|
| 'Paseante Noir' | 3/17 | 5/5 | 7/17 | 8/9 |
| 'Cabernet Sauvignon' | 3/24 | 5/7 | 7/21 | 8/30 |
| 'Pinot Noir' | 3/10 | 4/30 | 7/9 | 8/9 |

Table 2 presents the average cluster and berry data for 'Paseante Noir' and averaged over multiple years.

TABLE 2

Average cluster and berry sizes of 'Paseante Noir' and its comparison varieties. Data are averages over multiple years.

| Genotype | Number of Years | Avg. Cluster Wt. (g) | t-test Cluster Wt. | Avg. Berry Wt. (g) | t-test Berry Wt. | Clusters |
|---|---|---|---|---|---|---|
| 'Paseante Noir' | 7 | 294 | ab | 1.3 | abc | Loose |
| 'Blanc du Bois' | 6 | 148 | d | 1.5 | a | Well-filled |
| 'Cabernet Sauvignon' | 6 | 132 | d | 1.2 | c | Loose to well-filled |
| 'Chardonnay' | 6 | 196 | cd | 1.5 | ab | Well-filled to compact |
| 'Lenoir' | 6 | 157 | d | 1.3 | bc | Loose |

Table 3 presents the average yield per vine data taken over 2016 to 2018.

TABLE 3

Average production data for 'Paseante Noir' and its comparison varieties. Data are averages from three years (2016 to 2018).

| Genotype | Avg. Yield/ Vine (kg) | Std. Dev. (kg) | t-test | Number of Years |
|---|---|---|---|---|
| 'Paseante Noir' | 10.0 | 0.9 | a | 3 |
| 'Blanc du Bois' | 12.7 | 1.8 | a | 3 |
| 'Cabernet Sauvignon' | 10.9 | 1.8 | a | 3 |
| 'Chardonnay' | 10.9 | 3.2 | a | 3 |
| 'Lenoir' | 20.0 | 6.8 | b | 3 |

Mean berry juice data were also taken and Table 4 presents this data over a five-year period between 2014 and 2018. These values are consistent with cultivars that produce high quality wines.

TABLE 4

Average juice data for 'Paseante Noir' and its comparison varieties. Data are averages from five years (2014 to 2018).

| Genotype | Avg. °Brix | t-test Avg. °Brix | Avg. pH | t-test Avg. pH | Avg. titratable acidity (g/L) | t-test Avg. TA | Avg. L-malic acid (g/L) | t-test Avg. MA |
|---|---|---|---|---|---|---|---|---|
| 'Paseante Noir' | 27.5 | ab | 3.78 | ab | 5.0 | e | 1.6 | d |
| 'Blanc du Bois' | 23.5 | c | 3.58 | bc | 5.2 | de | 2.3 | bcd |
| 'Cabernet Sauvignon' | 25.8 | b | 3.74 | abc | 5.2 | de | 1.9 | bcd |
| 'Chardonnay' | 23.3 | cd | 3.68 | bc | 5.9 | cd | 2.4 | bc |
| 'Lenoir' | 21.3 | e | 3.96 | a | 9.1 | a | 4.5 | a |

*Xylella fastidiosa* susceptibility data are presented in Table 5, which presents the levels of *X. fastidiosa* in relationship to tolerant ('Blanc du Bois' and to a lesser extent, 'Lenoir') and susceptible ('Chardonnay' and 'Cabernet Sauvignon') cultivars. These are also mean data from repeated testing over seasons and greenhouses. Because of the high variation in greenhouse conditions, at least four standards (bio-controls) were always used: 'b43-17', 'Blanc du Bois', 'Lenoir', and 'Chardonnay' (and occasionally other *V. vinifera* cultivars), which allows the data to be compared across greenhouses, tests and seasons. These varieties tend to be very consistent in the amounts of bacteria they support as well as the severity of their disease expression. The cut-off between resistant and susceptible is usually between 75,000 and 250,000 colony forming units per milliliter (cfu/ml).

TABLE 5

*Xylella fastidiosa* concentrations based on ELISA readings and converted to colony forming units (cfu/ml). *Vitis arizonica* 'b43-17' is the source of resistance in the breeding program.

| Cultivar | Geometric Mean cfu/ml | t-test | Least Sq. Mean | Std. Error | Number of Times Tested |
|---|---|---|---|---|---|
| 'b43-17' | 12423 | a | 9.4 | 0.2 | 11 |
| 'Paseante Noir' | 73318 | b | 11.2 | 0.3 | 5 |
| 'Blanc du Bois' | 859096 | c | 13.7 | 0.2 | 11 |
| 'Lenoir' | 2421748 | d | 14.7 | 0.6 | 2 |
| 'Chardonnay' | 5197228 | d | 15.5 | 0.2 | 11 |
| 'Cabernet Sauvignon' | 6582993 | d | 15.7 | 0.8 | 1 |

Table 6 presents the phenotype of 'Paseante Noir'. The variety has normal hermaphroditic flowers and typical floral development as is found in commercial *V. vinifera* wine grapes.

| | 'Paseante Noir' |
|---|---|
| Berry L, W | 1.5 cm × 1.7 cm |
| Berry weight, shape | 1.1 g/round |
| Seed number, length and width typical for *V. vinifera* wine grapes, but not measured | 2 |
| Cluster L, W, shape, compactness, 2 clusters/shoot | 21.0 cm × 28.0 cm, long conical, some winged, loose |
| Pruning weights | 2.55 kg |
| Trunk width at 30 cm | 4.5 cm |
| Trunk color and texture | Rough shaggy bark 178D |
| Woody shoots diameter above cluster/and internode length | 0.8 cm/7.0 cm |
| Woody shoot texture and color | First year bark adheres but peels in strips in second year 164B |
| Active shoot color, internode color above the cluster zone/cluster zone shoot diameter/internode length (shoots same size as woody canes in the cluster zone) | 142D N144D 0.8 cm/7.0 cm |
| Tendril length, diameter | 6.5 cm 0.2 cm |
| Tendril color, Opposite leaves and alternating 2 nodes skip 2 nodes skip | 144C |
| Seed color | 164B |
| # Berries/cluster | 320 |
| Berry color skin and waxy bloom | 203D 190D |
| Leaves L, W | 23.0 cm × 20.0 cm |
| Leaf arrangement, leaf shape, and leaf color Top/Bottom | Alternate, palmate with 5 lobes 141C/142B |
| Petiole L, diameter, texture | 12.0 cm 0.4 cm smooth |
| Petiole color | 71A |
| Shoot tip color (first opened leaf) | 141C |
| Harvest date | Aug. 20 |
| Peduncle L, diam., color, texture | 4.5 cm 0.5 cm N144B Smooth |

Flower Descriptions

The floral buds and flower clusters are formed within the latent (dormant) bud in the year before flowering. As the pre-formed nodes on the compressed stems within the latent bud expand and the flower clusters begin developing and the individual flowers on the panicle begin forming. They are very small 2-4 mm and closer to 2 mm with wine grapes.

Leaf Descriptions

Rounded cuneiform leaves with rounded lateral lobes, shallow overlapping lateral sinuses, overlapping closed petiolar sinus, short rounded teeth, moderately dense tomentum on adaxial surface, red-purple (N78B) petioles which diffuses into the main veins

Fruit and Juice Parameters

YAN is yeast assimilable nitrogen and helps predict fermentation success. Seed color is rated as green to brown for mature seeds.

Berry Descriptions

The variety is not a "slip-skin" type grapes. They have skin that adheres to the flesh tightly. They are not firm at ripeness and are soft compared to modern era table grapes at harvest. The pedicels have normal attachment to the berries and are not distinguishable from other *V. vinifera* wine grapes in this or other morphological features, nor in juice and wine analysis.

Table 7 presents the wine characteristics of 'Paseante Noir'.

| | °Brix | TA (g/L) | pH | L-malic acid (g/L) | Potassium (mg/L) |
|---|---|---|---|---|---|
| 'Paseante Noir' | 24.4 | 4.6 | 3.75 | 1.11 | 2050 |

| | YAN (mg/L, as N) | Catechin (mg/L) | Tannin (mg/L) | Total anthocyanins (mg/L) |
|---|---|---|---|---|
| 'Paseante Noir' | 298 | 8 | 569 | 1556 |

Table 8 presents the juice, fruit and seed phenotype of 'Paseante Noir'.

| | Juice Hue | Juice Intensity | Juice Flavor | Skin Flavor |
|---|---|---|---|---|
| 'Paseante Noir' | red | med | fruity, spicy | ripe jam, plum |
| | Skin Tannin (1 = low, 4 = high) | Seed Color (1 = gr, 4 = br) | Seed Flavor | Seed Tannin (1 = high, 4 = low) |
| 'Paseante Noir' | 3 | 3 | nutty, slightly bitter | 2 |

'Paseante Noir' has excellent PD resistance. However, it is highly susceptible to a wide range of pests and diseases in a manner similar to other *V. vinifera* cultivars, and thus it must be treated as a pure *V. vinifera* cultivar in terms of susceptibility to fungal diseases and pests. 'Paseante Noir' has no known tolerance to adverse weather. Plants observed were found to be true to type through successive generations of asexual reproductions.

What is claimed is:

1. A new and distinct variety of grapevine plant designated 'Paseante Noir' as shown and described herein.

* * * * *

| Marker Alleles for the International Set of SSR Loci for Fingerprinting Grape | | | | | | | | | | | | | | | | | | | | |
|---|---|---|---|---|---|---|---|---|---|---|---|---|---|---|---|---|---|---|---|---|
| Cultivar | VVMD5 | | VVMD7 | | VVS2 | | VrZAG79 | | VrZAG62 | | VVMD31 | | VVMD27 | | VVMD32 | | VVIP26 | | CH14-77 | |
| Paseante Noir | 229 | 229 | 235 | 245 | 130 | 138 | 246 | 254 | 190 | 196 | 210 | 212 | 175 | 185 | 237 | 261 | 146 | 160 | 178 | 202 |
| Riesling | 226 | 235 | 235 | 235 | 134 | 146 | 242 | 242 | 184 | 190 | 202 | 206 | 169 | 183 | 237 | 237 | 160 | 166 | 178 | 178 |
| Alicante Bouschet | 220 | 233 | 235 | 239 | 128 | 140 | 238 | 252 | 184 | 184 | 208 | 208 | 175 | 188 | 247 | 269 | 154 | 160 | 178 | 178 |
| Chenin blanc | 220 | 226 | 235 | 249 | 128 | 128 | 240 | 246 | 192 | 196 | 212 | 212 | 183 | 185 | | | 160 | 160 | 178 | 185 |
| Zinfandel | 220 | 230 | 243 | 245 | 128 | 138 | 232 | 254 | 196 | 200 | 208 | 210 | 173 | 175 | 253 | 261 | 160 | 160 | 178 | 178 |
| Touriga Nacional | 220 | 220 | 235 | 235 | 138 | 146 | 240 | 240 | 184 | 190 | 200 | 212 | 175 | 183 | 237 | 269 | 140 | 154 | 168 | 178 |
| Semillon | 233 | 235 | 235 | 245 | 132 | 138 | 234 | 238 | 190 | 200 | 210 | 212 | 175 | 179 | 237 | 247 | 154 | 160 | 178 | 178 |
| Palomino | 220 | 220 | 239 | 243 | 128 | 128 | 250 | 254 | | | 200 | 212 | 173 | 175 | 253 | 259 | 154 | 160 | 178 | 178 |
| Chardonnay | 229 | 233 | 235 | 239 | 132 | 138 | 238 | 240 | 184 | 192 | 210 | 212 | 175 | 183 | 237 | 269 | 154 | 180 | 178 | 178 |
| Cabernet Sauvignon | 226 | 235 | 235 | 235 | 134 | 146 | 242 | 242 | 184 | 190 | 202 | 206 | 169 | 183 | 237 | 237 | 160 | 166 | 178 | 178 |

FIG. 1